(12) United States Patent
Madhyastha

(10) Patent No.: US 8,906,364 B2
(45) Date of Patent: *Dec. 9, 2014

(54) ANTIMICROBIAL COMPOSITIONS AND USES THEREOF

(75) Inventor: Srinivasa Madhyastha, Winnipeg (CA)

(73) Assignee: Kane Biotech Inc., Winnipeg (CA)

( * ) Notice: Subject to any disclaimer, the term of this patent is extended or adjusted under 35 U.S.C. 154(b) by 1740 days.

This patent is subject to a terminal disclaimer.

(21) Appl. No.: 11/331,423

(22) Filed: Jan. 11, 2006

(65) Prior Publication Data

US 2007/0003538 A1  Jan. 4, 2007

Related U.S. Application Data

(60) Provisional application No. 60/695,546, filed on Jul. 1, 2005, provisional application No. 60/742,972, filed on Dec. 6, 2005.

(51) Int. Cl.
| | | |
|---|---|---|
| A61K 38/47 | (2006.01) | |
| A61K 31/155 | (2006.01) | |
| A61L 29/16 | (2006.01) | |
| A01N 47/44 | (2006.01) | |
| A61L 2/16 | (2006.01) | |
| A61L 2/18 | (2006.01) | |
| A61L 2/22 | (2006.01) | |
| A61L 12/08 | (2006.01) | |
| A61L 12/14 | (2006.01) | |
| A61L 27/34 | (2006.01) | |
| A61L 29/04 | (2006.01) | |
| A61L 29/08 | (2006.01) | |
| A61K 38/17 | (2006.01) | |

(52) U.S. Cl.
CPC .............. *A61L 29/16* (2013.01); *A01N 47/44* (2013.01); *A61K 31/155* (2013.01); *A61L 2/16* (2013.01); *A61L 2/18* (2013.01); *A61L 2/22* (2013.01); *A61L 12/082* (2013.01); *A61L 12/141* (2013.01); *A61L 12/145* (2013.01); *A61L 27/34* (2013.01); *A61L 29/044* (2013.01); *A61L 29/085* (2013.01); *A61K 38/17* (2013.01); *A61L 2300/206* (2013.01); *A61L 2300/252* (2013.01); *A61L 2300/404* (2013.01); *A61L 2300/42* (2013.01)

USPC .......... 424/94.61; 514/635; 514/2.3; 424/422; 604/523; 623/1.26; 623/1.46

(58) Field of Classification Search
None
See application file for complete search history.

(56) References Cited

U.S. PATENT DOCUMENTS 3,170,840 A * 2/1965 Timm ................ 424/201.1
5,019,096 A   5/1991 Fox, Jr. et al.
(Continued)

FOREIGN PATENT DOCUMENTS

WO   WO 2005/018701 A1   3/2005

OTHER PUBLICATIONS

Soboh et al. "Effects of Ciprofloxacin and Protamine Sulfate Combinations against Catheter-Associated *Pseudomonas aeruginosa* Biofilms" Antimicrobial Agents and Chemotherapy, Jun. 1995, 1281-1286.*

(Continued)

*Primary Examiner* — Rachael E Bredefeld
*Assistant Examiner* — Dominic Lazaro
(74) *Attorney, Agent, or Firm* — David J. Heller; Ridout & Maybee LLP

(57) ABSTRACT

The present invention provides compositions for preventing growth and proliferation of biofilm embedded microorganisms on devices comprising: (a) a cationic polypeptide and (b) a bis-guanide or a salt thereof. The invention further provides methods for preparing medical devices with such compositions.

13 Claims, 8 Drawing Sheets

(56) References Cited

U.S. PATENT DOCUMENTS

| | | | |
|---|---|---|---|
| 5,089,205 | A | 2/1992 | Huang et al. |
| 5,165,952 | A | 11/1992 | Solomon et al. |
| 5,362,754 | A | 11/1994 | Raad et al. |
| 5,451,424 | A * | 9/1995 | Solomon et al. ............... 427/2.1 |
| 5,616,338 | A | 4/1997 | Fox, Jr. et al. |
| 5,688,516 | A | 11/1997 | Raad et al. |
| 6,187,768 | B1 | 2/2001 | Welle et al. |
| 6,261,271 | B1 | 7/2001 | Solomon et al. |
| 6,589,591 | B1 | 7/2003 | Mansouri et al. |
| 6,706,024 | B2 | 3/2004 | Modak et al. |
| 6,843,784 | B2 | 1/2005 | Modak et al. |
| 7,329,412 | B2 | 2/2008 | Modak et al. |
| 2003/0044446 | A1 * | 3/2003 | Moro et al. .................. 424/426 |

OTHER PUBLICATIONS

Kim et al., "Synergistic Inhibitory Effect of Cationic Peptides and Antimicrobial Agents on the Growth of Oral Streptococci", *Caries Res.*, 37:425-430 (2003).

Darouiche, R. et al. "Antimicrobial activity and durability of a novel antimicrobial-impregnated bladder catheter," International Journal of Antimicrobial Agents, 8:243-247, 1997.

Darouiche, R. et al. "A comparison of two antimicrobial-impregnated central venous catheters. Catheter study group," New England Journal of Medicine, 340(1):1-8, Jan. 7, 1999.

Darouiche, R. et al. "Efficacy of antimicrobial-impregnated bladder catheters in reducing catheter-associated bacteriuria: a prospective, randomized, multicenter clinical trial," Urology, 54(6):976-981, 1999.

Fallgren, C. et al. "In vitro Anti-Staphylococcal Activity of Heparinized Biomaterials bonded with Combinations of Rifampicin," Zent. BL. Bakteriol, 287:19-31, 1998.

Johnson, J. et al. "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, 43(12):2990-2995, Dec. 1999.

Kim, C. et al. "Evaluation of an antimicrobial-impregnated continuous ambulatory peritoneal dialysis catheter for infection control in rats," American Journal of Kidney Disease, 39(1):165-173, Jan. 2002.

Raad, I. et al. Minocycline and Ethylenediaminetetraacetate for the Prevention of Recurrent Vascular Catheter Infections, Clinical Infectious Diseases, 25:149-151, 1997.

Raad, I. et al. "Antimicrobial durability and rare ultrastructural colonization of indwelling central catheters coated with minocycline and rifampin," Critical Care Medicine, 26(2):219-224, Feb. 1998.

Richards, G. et al. "The Effect of Protamine on Antibiotic Action Against *Staphylococus epidermidis* Biofilms," Asaio Transactions, 36:296-299, 1990.

Schierholz, J. et al. "Controlled release of antibiotics from biomedical polyurethanes: morphological and structural features," Biomaterials, 18(12):839-844, 1997.

Sherertz, R. et al. "Efficacy of Dicloxacillin-Coated Polyurethane Catheters in Preventing Subcutaneous *Staphylococcus aureus* Infection in Mice," Antimicrobial Agents and Chemotherapy, 33(8):1174-1178, Aug. 1989.

Soboh, F. et al. "Effects of Ciprofloxacin and Protamine Sulfate Combinations against Catheter-Associated *Pseudomonas aeruginosa* Biofilms," Antimicrobial Agents and Chemotherapy, 39(6):1281-1286, Jun. 1995.

Stickler, D. "Biomaterials to prevent nosocomial infections: is silver the gold standard?" Current Opinion in Infectious Disease, 13:389-393, 2000.

Tunney, M. et al. "Infection associated with medical devices," Reviews in Medical Microbiology, 7(4):195-205, 1996.

Burton et al., "Antibiofilm activity of GlmU enzyme inhibitors against catheter-associate uropathogens," *Antimicrob. Agents Chemother.* 50: 1835-1840, 2006.

Kuyyakanond, T. and Quesnel, K.B., "The mechanism of action of chlorhexidine," *FEMS Microbiol. Lett.* 100: 211-216 (1992).

Yakandawala et al., "Effect of ovotransferrin, protamine sulfate, and EDTA combination on biofilm formation by catheter associated bacteria," *J. Appl. Microbiol.* 102: 722-727 (2007).

Gilbert, P. & Allison, D.G., "Preservation of Pharmaceutical Products" in *Encyclopedia of Pharmaceutical Technology* (3rd Edition), p. 2983-2992 (Oct. 2, 2006). DOI: 10.1081/E-EPT-100200009.

Karpanen et al., "Antimicrobial efficacy of chlorhexidine digluconate alone and in combination with eucalyptus oil, tea tree oil, and thymol against planktonic and biofilm cultures of *Streptococcus epidermis*," *J. Antimicrob. Chemother.* 62: 1031-1036 (2008).

Logghe, C. et al., "Evaluation of chlorhexidine and silver-sulfadiazine impregnated central venous catheters for the prevention of bloodstream infection in leukaemic patients: a randomized controlled trial," *J. Hosp. Infect.* 37: 145-156 (1997).

Pons et al., "Evaluation of antimicrobial interactions between chlorhexidine, quarternary ammonium compounds, preservatives, and excipients," *J. Appl. Bacteriol.* 73: 395-400 (1992).

Mavroldi et al., Ciprofloxacin-resistant *Escherichia coli* in Central Greece: mechanisms of resistance and molecular identification, BMC Infectious Diseases 2012, 12:371.

Guillermo et al., In Vitro Antimocrobial Resistance of Urinary *Escherichia coli* Isolates among U.S. Outpatients from 2000 to 2010, Antimicrob. Agents Chemother. 2012, 56(4):2181.

Jacoby, Mechanisms of Resistance of Quinolones, Clinical Infections Diseases 2005, 41:S120-6.

Braydich-Stolle et al. In Vitro Cytotoxicity of Nanoparticles in Mammalian Germline Stem Cells, Toxicol. Sci. 2005, 88 (2):412-419.

DuToit et al., An in vitro evaluation of the cell toxicity of honey and silver dressings, Journal of Wound Care 2009, 18(9) pp. 383-389.

Lansdown, A Pharmacological and Toxicological Profile of Silver as an Antimicrobial Agent in Medical Devices, Advances in Pharmacological Sciences 2010, Article ID910686.

Richards et al., The Effect of Protamine on Antibiotic Action Against *Staphylococcus epidermidis* Biofilms, ASAIO Transactions 1990, 36: M296-M299.

Yakandawala et al., Effect of ovotransferrin, protamine sulfate and EDTA combination on biofilm formation by catheter-associated associated bacteria, Journal of Applied Microbiology 2007, 102:722-727.

Pons et al., Evaluation of antimicrobial interactions between chlorhexidine, quaternary ammonium compounds, preservatives and excipients, Journal of Applied Bacteriology 1992, 73: 395-400.

Karpanen et al., Antimicrobial efficacy of chlorhexidine digluconate alone and in combination with eucalyptus oil, tea tree oil and thymol against planktonic and biofilm cultures of *Staphylococcus epidermidis*, Journal of Antimicrobial Chemotherapy 2008, 62: 1031-36.

Domenico et al., BisEDT and RIP act in synergy to prevent graft infections by resistant staphylococci, Peptides 2004, 25: 2047-2053.

Aslam et al., Combination of Tigecycline and N-Acetylcysteine Reduces Biofilm-Embedded Bacteria on Vascular Catheters, Antimicrobial Agents and Chemotherapy 2007, 51: 1556-1558.

Ammons et al., In vitro susceptibility of established biofilms composed of clinical wound isolate of *Pseudomonas aeruginosa* treated with lactoferrin and xylitol, International Journal of Microbial Agents 2009, 33: 230-236.

Percival et al., Bacterial resistance to silver in wound care, Journal of Hospital Infection 2005, 60: 1-7.

* cited by examiner

ANTIMICROBIAL COMPOSITIONS AND USES THEREOF

CROSS REFERENCE TO RELATED APPLICATIONS

This application claims the benefit under 35 U.S.C. §119(e) of U.S. Provisional Application No. 60/695,546, filed Jul. 1, 2005, and U.S. Provisional Application No. 60/742,972, filed Dec. 6, 2005, the entire disclosures of which are hereby incorporated by reference.

FIELD OF THE INVENTION

The present invention relates to antimicrobial compositions that inhibit growth and proliferation of biofilm embedded microorganisms on or in devices, and in particular medical devices such as catheters.

BACKGROUND

Urinary tract infection (UTI) is the most common hospital-acquired infection, accounting for up to 40% of all nosocomial infections. The majority of cases of UTI are associated with the use of urinary catheters, including trans-urethral foley, suprapubic, and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTI continues to pose a major problem. For instance, it is estimated that almost one-quarter of hospitalized spinal cord-injured patients develop symptomatic UTI during their hospital course. Gram-negative bacilli account for almost 60-70%, *Enterococci* for about 25%, and *Candida* species for about 10% cases of catheter-associated UTI. Furthermore, indwelling medical devices including vascular catheters are becoming essential in the management of hospitalized patients by providing venous access. The benefit derived from these catheters as well as other types of medical devices such as peritoneal catheters, cardiovascular devices, orthopedic implants, and other prosthetic devices is often offset by infectious complications. The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. *Candida albicans*, a fungal agent, accounts for 10-15% of catheter infections.

In recent years, there have been numerous efforts to sequester antimicrobials and antibiotics on the surface of or within devices that are then placed in the vasculature or urinary tract as a means of reducing the incidence of device-related infections. These antimicrobial agents are of varying chemical composition and can include cationic polypeptides (protamine, polylysine, lysozyme, etc.), antiseptics (chlorhexidine, triclosan, etc.), surfactants (sodium dodecyl sulfate, Tween®-80, surfactin, etc.), quaternary ammonium compounds (benzalkonium chloride, tridodecyl methyl ammonium chloride, didecyl dimethyl ammonium chloride, etc.), silver ions/compounds, and nitrofurazone.

The main methods of antimicrobial catheter preparation include immersion or flushing, coating, drug-polymer conjugate and impregnating (Tunney et al., *Rev. Med. Microbiol.*, 7(4): 195-205, 1996). In a clinical setting, suitable catheters can be treated by immersion immediately prior to placement, which offers flexibility and control to clinicians in certain situations. Several studies have examined the clinical efficacy of catheters coated with antimicrobial agents. Polyurethane catheters coated with minocycline and EDTA showed potential in reducing recurrent vascular catheter-related infections (Raad et al., *Clin. Infect. Dis.*, 25:149-151, 1997). Minocycline and rifampin coatings have been shown to significantly reduce the risk of catheter-associated infections (Raad et al., *Crit. Care Med.*, 26:219-224, 1998). Minocycline coated onto urethral catheters has been shown to provide some protection against colonization (Darouiche et al., *Int. J. Antimicrob. Ag.*, 8:243-247, 1997). Johnson et al. described substantial in vitro antimicrobial activity of a commercially available nitrofurazone coated silicone catheter (*Antimicrob. Agents Chemother.*, 43:2990-2995, 1999). The antibacterial activity of silver-containing compounds as antimicrobial coatings for medical devices has been widely investigated. Silver-sulfadiazine used in combination with chlorhexidine has received particular interest as a central venous catheter coating (Stickler, *Curr. Opin. Infect. Dis.*, 13:389-393, 2000; Darouiche et al., *New Eng. J. Med.*, 340: 1-8, 1999).

The loading of antimicrobial agents into medical devices by immersion or coating technologies has the advantage of being relatively simple. However, the limited mass of drug that can be incorporated may be insufficient for a prolonged antimicrobial effect, and the release of the drug following clinical insertion of the device is rapid and relatively uncontrolled. A means of reducing these problems is by direct incorporation of the antimicrobial agent into the polymeric matrix of the medical device at the polymer synthesis stage or at the device manufacture stage. Rifampicin has been incorporated into silicone in an attempt to prevent infection of cerebrospinal fluid shunts with some success (Schierholz et al., *Biomaterials,* 18:839-844, 1997). Iodine has also been incorporated into medical device biomaterials. Coronary stents have been modified to have antithrombogenic and antibacterial activity by covalent attachment of heparin to silicone with subsequent entrapment of antibiotics in cross-linked collagen bound to the heparinized surface (Fallgren et al., *Zentralbl. Bakteriol.,* 287:19-31, 1998).

Welle et al. disclosed the method of preparing a kit for flushing a medical device (U.S. Pat. No. 6,187,768). The kit includes a solution containing an antibiotic, an anticoagulant (protamine sulfate) and an antithrombotic agent or chelating agent useful for preventing infections caused by bacterial growth in catheters.

Raad et al. disclosed that pharmaceutical compositions of a mixture of minocycline and EDTA were useful in maintaining the patency of a catheter port (U.S. Pat. No. 5,362,754). Recently, Raad and Sheretz further disclosed that effective catheter flush solutions could be prepared with non-glycopeptide antimicrobial agent, an antithrombic agent, an anticoagulant, and a chelating agent selected from the group consisting of EDTA, EGTA and DTPA (U.S. Pat. No. 5,688,516).

Welle et al. teach the use of several anticoagulants for use in medical devices, including protamine sulfate (U.S. Pat. No. 6,187,768). Combinations of protamine sulfate and certain antibiotics have been shown to have synergistic effects on catheter-associated bacteria such as *Pseudomonas aeruginosa* and *Staphylococcus epidermidis* (Soboh et al., *Antimicrob. Agents. Chemother.*, 39: 1281-1286, 1995; Richards et al., *ASAIO Trans,* 36:296-299). Kim et al. (*Am. J. Kidney Dis.,* 39: 165-173, 2002) developed an antimicrobial-impregnated peritoneal dialysis catheter by impregnating the cuff and tubing with chlorhexidine, silver-sulfadiazine and triclosan in a polymer matrix. Fox et al. disclose medical devices having the synergistic composition comprising a silver salt and chlorhexidine (U.S. Pat. No. 5,019,096). Soloman et al. disclose anti-infective medical articles containing chlorhexidine (U.S. Pat. No. 6,261,271). Modak et al., in U.S. Pat. Nos. 6,706,024 and 6,843,784, disclose chlorhexidine, triclosan, and silver compound containing medical devices.

SUMMARY OF THE INVENTION

An embodiment of the present invention provides a composition for preventing growth and proliferation of biofilm embedded microorganisms on a device, said composition comprising: (a) a cationic polypeptide and (b) a bis-guanide or a salt thereof.

In an embodiment of the invention, the cationic polypeptide is between about 12.5 mg/ml and about 100 mg/ml of the composition.

In another embodiment of the invention, the bis-guanide is between about 100 mg/ml and about 400 mg/ml of the composition.

In a further embodiment, the composition according to the invention is effective for preventing growth and proliferation of biofilm embedded bacteria.

Bacteria may include, but not limited to, gram-negative bacteria such as *Escherichia coli, Proteus mirabilis, Klebsiella pneumoniae, Pseudomonas aeruginosa, Klebsiella oxytoca, Providentia stuartii*, and *Serratia marcescens*.

Bacteria may include, but not limited to, gram-negative bacteria such as *Enterococcus faecalis*, Vancomycin Resistant *Enterococci* (VRE), *Streptococcus viridans, Staphylococcus epidermidis, Staphylococcus aureus*, and *Staphylococcus saprophyticus*.

In another embodiment, a composition is effective for preventing growth and proliferation of biofilm embedded fungus, which may include *Candida albicans*.

In a further embodiment, the cationic polypeptide is selected from the group consisting of protamine sulfate, defensin, lactoperoxidase, and lysozyme.

In a still further embodiment, the bis-guanide is selected from the group consisting of chlorhexidine, alexidine, and polymeric bis-guanides.

In a still further embodiment, the bis-guanide is a chlorhexidine salt.

The chlorhexidine salt may be selected from the group consisting of chlorhexidine diglucanate, chlorhexidine diacetate, and chlorhexidine dihydrochloride.

In a further embodiment, the cationic polypeptide is protamine sulfate and the bis-guanide is a chlorhexidine salt.

In a still further embodiment, a composition comprises about 100 mg/ml protamine sulfate and about 400 mg/ml chlorhexidine salt.

In yet a further embodiment, a composition according to the invention further comprises one or more ingredients such as water; a binding, bonding or coupling agent or cross-linking agent; a bis-phenol; a quaternary ammonium compound; a maleimide; an antibiotic; and a pH adjuster.

In another aspect, the present invention provides a method of preparing a device comprising treating at least one surface of the device with a composition according to the methods disclosed herein.

In a further aspect, the present invention provides a method of preparing a device comprising incorporating a composition according to the invention into polymers, which are used to form the device.

In another aspect, the present invention provides a method of preparing a device comprising coating a composition according to the invention onto at least one surface of the device.

In an embodiment, the composition comprises effective amounts of protamine sulfate and chlorhexidine salt.

In an embodiment of the invention, a device is a medical device.

In another embodiment of the invention, a device may be a catheter.

A catheter may be an indwelling catheter such as a central venous catheter, a peripheral intravenous catheter, an arterial catheter, a haemodialysis catheter, an umbilical catheter, percutaneous nontunneled silicone catheter, a cuffed tunneled central venous catheter, or a subcutaneous central venous port.

A catheter may be an indwelling catheter such as urinary catheter, a peritoneal catheter, or a central venous catheter In another embodiment, a device may include catheters, pacemakers, prosthetic heart valves, prosthetic joints, voice prostheses, contact lenses, or intrauterine devices.

In a further aspect, the invention provides a composition for preventing device-related infection, said composition comprising: (a) a cationic polypeptide and (b) a bis-guanide or a salt thereof.

In a further aspect, the invention provides a method of preparing a device comprising treating at least one surface of the device with (a) a cationic polypeptide and (b) a bis-guanide or a salt thereof.

In a further aspect, the invention provides a composition comprising (a) a cationic polypeptide, (b) a bis-guanide or a salt thereof, and (c) a medical device on which said cationic polypeptide and said bis-guanide or salt thereof is coated, incorporated, or treated.

In a further aspect, the invention provides the use of any of the compositions described herein in the preparation of a medical device for implantation in a mammal.

DETAILED DESCRIPTION

Figure 1:
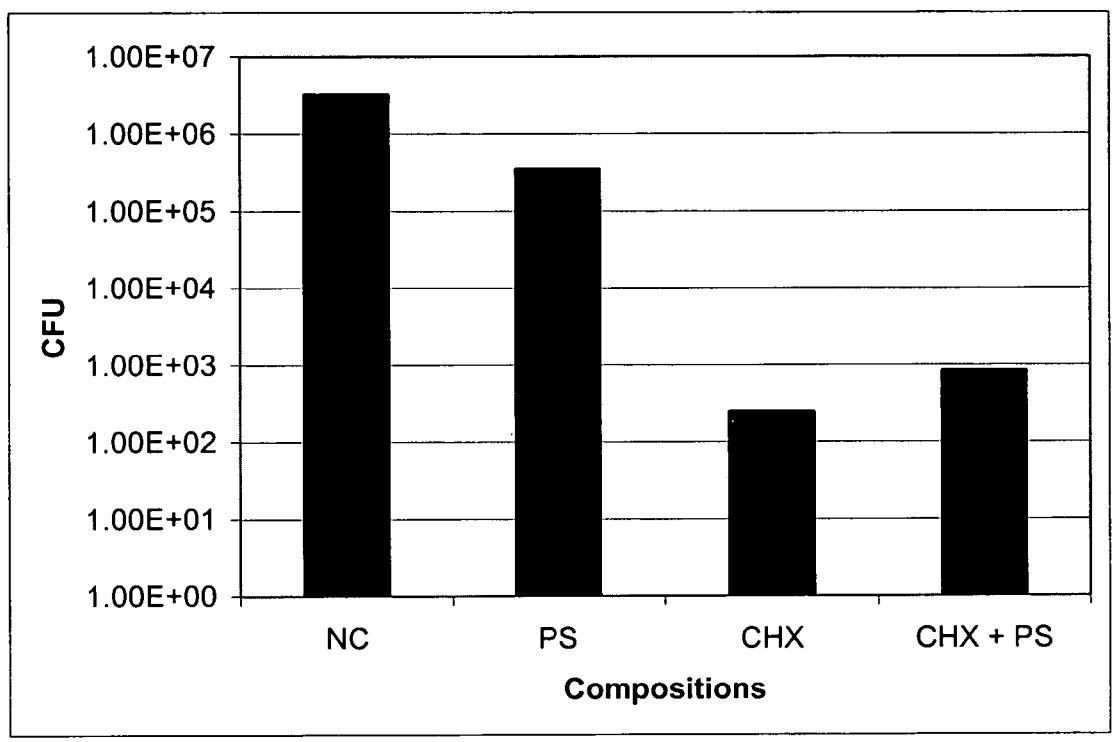
FIG. 1 is a bar graph illustrating the effect of a negative control (NC) (solution without an active ingredient), 50 μg/ml protamine sulfate (PS), 12.5 μg/ml chlorhexidine salt (CHX), and a combination of 50 μg/ml protamine sulfate and 12.5 μg/ml chlorhexidine salt (PS+CHX) on the number (CFU) of biofilm embedded *E. coli*.

Compositions comprising at least one cationic polypeptide and at least one bis-guanide have enhanced antimicrobial activity. In particular, such compounds are effective for preventing growth and proliferation of microorganisms, including both bacterial and fungal species, embedded in biofilms. An enhanced antimicrobial activity is evidenced by the small quantities of each of these compounds that need to be used to produce an effective antimicrobial composition. A necessary overall amount of the compounds is less than that which would be required if any of the compounds were to be used on their own. In particular, it is possible to use small amounts of a cationic polypeptide, which is biologically acceptable, and a small amount of bis-guanide, which is biologically acceptable at lower concentrations and are effective antimicrobials.

Accordingly, an embodiment of the present invention provides compositions for preventing growth and proliferation of biofilm embedded microorganisms comprising: (a) a cationic polypeptide and (b) a bis-guanide or salt thereof.

An embodiment of the present invention also provides compositions for preventing infection caused or exacerbated by implanted medical devices or catheters, such as urinary tract infections caused by indwelling catheters, by coating said medical devices or catheters with said composition, such composition comprising (a) a cationic polypeptide and (b) a bis-guanide or salt thereof.

A synergistic antimicrobial composition of the invention requires remarkably small amounts of active ingredients (compared to that which has been used in the past) to be effective. A composition according to the invention may have properties that include those of separate compounds but go beyond them in efficacy and scope of application. Extremely low levels, and hence increased efficacy, of active compounds or ingredients, make embodiments of this invention very desirable and relatively economical to manufacture, although higher concentrations of these compounds can be used if it is desired for certain applications. A further advantage of using these compositions is the effectiveness for preventing growth of biofilm embedded bacteria and fungus, and in particular, bacterial and fungal species that colonize medical devices such as catheters. Examples of cationic polypeptides useful for preparing compositions of the invention include, but are not limited to, protamine sulfate, defensin, lactoperoxidase, and lysozyme. In a preferred embodiment of the invention, the cationic polypeptide is protamine sulfate.

An amount of cationic polypeptide included in the composition is preferably between about 10 mg/ml to about 200 mg/ml and more preferably between about 12.5 mg/ml to about 100 mg/ml. The higher end of this range can be used to prepare a concentrated product which may be diluted prior to use.

Examples of bis-guanides useful for preparing the compositions of the invention include, but are not limited to chlorhexidine, alexidine, or polymeric bis-guanides. A bis-guanide may be in the form of a suitable salt. Bis-guanide salts are well known. In a preferred embodiment of the invention, the compositions are prepared using a chlorhexidine salt, and more preferably of chlorhexidine digluconate, chlorhexidine diacetate, or chlorhexidine dihydrochloride.

The amount of bis-guanide included in a composition is preferably between about 10 mg/ml to about 400 mg/ml and more preferably between about 100 mg/ml to about 400 mg/ml. The higher end of this range can be used to prepare a concentrated product that may be diluted prior to use.

Higher concentrations of a compound can be used for certain applications depending on targeted bacteria and a device to be treated. Suitable working concentrations can easily be determined using known methods.

In a preferred embodiment of the invention, the composition comprises protamine sulfate as the cationic polypeptide and a chlorhexidine salt as the bis-guanide. In a further preferred embodiment, the composition includes about 100 mg/ml of protamine sulfate and about 100 mg/ml of a chlorhexidine salt.

Compositions of the invention can be prepared using known methods. Generally, components are dissolved in a suitable solvent, such as water, glycerol, organic acids, and other suitable solvents Compositions of the invention may include any number of well known active components and base materials. Compositions may further comprise ingredients such as, but not limited to: suitable solvents such as water; antibiotics such antibacterials and antifungals; binding, bonding, or coupling agent, cross-linking agent; or a pH adjuster.

Compositions of the invention may further comprise additional antimicrobial ingredients such as bis-phenols, N-substituted maleimides, and quaternary ammonium compounds. Examples of bis-phenols useful for preparing compositions of the present invention include, but are not limited to, triclosan and hexachlorophene. Examples of N-maleimides useful for preparing compositions of the present invention include, but are not limited: to N-ethylmaleimide (NEM), N-phenylmaleimide (PheM), N-(1-pyrenyl) maleimide (PyrM), naphthalene-1,5-dimaleimide (NDM), N,N'-(1,2-phenylene)dimaleimide (oPDM), N,N'-1,4-phenylene dimaleimide (pPDM), N,N'-1,3-phenylene dimaleimide (mPDM), and 1,1-(methylenedi-4,1-phenylene)bismaleimide (BM). Examples of quaternary ammonium compounds useful for preparing compositions of the present invention include, but are not limited to benzalkonium chloride, tridodecyl methyl ammonium chloride, and didecyl dimethyl ammonium chloride.

Other possible components of the composition include, but are not limited to, buffer solutions, phosphate buffered saline, saline, polyvinyl, polyethylene, polyurethane, polypropylene, silicone (e.g., silicone lassoers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylaminoethyl methacrylate), poly-(dialkylaminomethyl styrene) or poly-(vinylpyridine), polyammonium ions (e.g., poly-(2-methacryloxyethyl trialkyl ammonium ion), poly-(vinylbenzyl trialkyl ammonium ions), poly-(N,N-alkylypyridinium ion) or poly-(dialkyloctamethylene ammonium ion) and polysulfonates (e.g. poly-(vinyl sulfonate) or poly-(styrene sulfonate), collodion, nylon, rubber, plastic, polyesters, Dacron® (polyethylene teraphthalate), Teflon® (polytetrafluoroethylene), latex, and derivatives thereof, elastomers and Dacron® (sealed with gelatin, collagen or albumin), cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above-exemplified polymers may also be used.

Examples of biofilm embedded bacteria that may be inhibited using compositions according to the invention include gram-negative bacteria such as, but not limited to: *Escherichia coli, Proteus mirabilis, Klebsiella pneumoniae, Pseudomonas aeruginosa, Klebsiella oxytoca, Providentia stuartii,* or *Serratia marcescens* and gram-positive bacteria such as, but not limited to: *Enterococcus faecalis,* Vancomycin Resistant *Enterococci* (VRE), *Streptococcus viridans, Staphylococcus epidermidis,* and *Staphylococcus aureus* or *Staphylococcus saprophyticus.* These bacteria are commonly found associated with medical devices including catheters.

Compositions according to the invention can also be used to inhibit the growth and proliferation of biofilm embedded fungi such as *Candida albicans, Candida parapsilosis,* and *Candida utilis.* In another aspect, the present invention provides a method of preparing a device comprising treating at least one surface of the device with a cationic polypeptide and bis-guanide composition according to the invention. In a preferred embodiment of the invention, a composition used to prepare a device comprises and effective amount of protamine sulfate as the cationic polypeptide and a chlorhexidine salt as the bis-guanide.

The term "effective" refers to a sufficient amount of active components to substantially prevent growth or proliferation of biofilm embedded microorganisms on at least one surface of a medical device coated with an embodied composition; and as a sufficient amount of the active components to substantially penetrate, or break-up, a biofilm on at least one surface of a medical device, thereby facilitating access of active components, antimicrobial agents, and/or antifungal agents to microorganisms embedded in a biofilm, and thus, removal of substantially all microorganisms from at least one surface of a medical device treated with a solution of an embodied composition. An amount will vary for each active component and upon known factors such as pharmaceutical characteristics; type of medical device; degree of biofilm embedded microorganism contamination; and use and length of use.

Examples of devices that can be treated using the compositions of the invention include medical devices such as tubing and other medical devices, such as catheters, pacemakers, prosthetic heart valves, prosthetic joints, voice prostheses, contact lenses, and intrauterine devices.

Medical devices include disposable or permanent or indwelling catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device which may be inserted or implanted into a human being or other animal, or placed at the insertion or implantation site such as the skin near the insertion or implantation site, and which include at least one surface which is susceptible to colonization by biofilm embedded microorganisms.

Medical devices for the present invention include surfaces of equipment in operating rooms, emergency rooms, hospital rooms, clinics, and bathrooms.

Implantable medical devices include orthopedic implants, which may be inspected for contamination or infection by biofilm embedded microorganisms using endoscopy. Insertable medical devices include catheters and shunts, which can be inspected without invasive techniques such as endoscopy.

Medical devices may be formed of any suitable metallic materials or non-metallic materials. Examples of metallic materials include, but are not limited to, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gore-Tex® (polytetrafluoroethylene), Dacron® (polyethylene tetraphthalate), Teflon® (polytetrafluoroethylene), latex, elastomers, and Dacron® sealed with gelatin, collagen, or albumin, and derivatives or combinations thereof.

In a preferred embodiment, the method of treating at least one surface of a medical device comprises contacting a medical device with a composition according to the invention. As used herein, the term "contacting" includes, but is not limited to: coating, spraying, soaking, rinsing, flushing, submerging, and washing. A medical device is contacted with a composition for a period of time sufficient to remove substantially all biofilm embedded microorganisms from a treated surface of a medical device.

In a more preferred embodiment, a medical device is submerged in a composition for at least 5 minutes. Alternatively, a medical device may be flushed with a composition. In the case of a medical device being tubing, such as dental drain tubing, a composition may be poured into a dental drain tubing and both ends of the tubing clamped such that the composition is retained within the lumen of the tubing. The tubing is then allowed to remain filled with the composition for a period of time sufficient to remove substantially all of the microorganisms from at least one surface of the medical device, generally, for at least about 1 minute to about 48 hours. Alternatively, tubing may be flushed by pouring a composition into the lumen of the tubing for an amount of time sufficient to prevent substantial growth of all biofilm embedded microorganisms. Concentrations of active components in a composition may vary as desired or necessary to decrease the amount of time the composition is in contact with a medical device.

In another embodiment of a method for treating a surface of a device, a composition of the invention may also include an organic solvent, a medical device material penetrating agent, or adding an alkalinizing agent to the composition, to enhance reactivity of a surface of the medical device with the composition. An organic solvent, medical device material penetrating agent, and/or alkalinizing agent are those which preferably facilitate adhesion of a composition to at least one surface of a medical device.

Another aspect provides a method of coating a composition of the invention onto at least one surface of a device. Preferably, the device is a medical device. Broadly, a method for coating a medical device includes steps of providing a medical device; providing or forming a composition coating; and applying the composition coating to at least one surface of the medical device in an amount sufficient to substantially prevent growth or proliferation of biofilm embedded microorganisms on at least one surface of the medical device. In one specific embodiment, a method for coating a medical device includes steps of forming a composition of the invention of an effective concentration for activating an active component, thereby substantially preventing growth or proliferation of microorganisms on at least one surface of the medical device, wherein the composition of the invention is formed by combining an active component and a base material. At least one surface of a medical device is then contacted with a composition of the invention under conditions wherein the composition of the invention covers at least one surface of the medical device. The term "contacting" further includes, but is not limited to: impregnating, compounding, mixing, integrating, coating, spraying and dipping.

In another embodiment of a method for coating a medical device, a composition coating is preferably formed by combining an active component and a base material at room temperature and mixing the composition for a time sufficient to evenly disperse active agents in the composition prior to applying the composition to a surface of the device. A medical device may be contacted with a composition for a period of time sufficient for a composition to adhere to at least one surface of the device. After a composition is applied to a surface of a device, it is allowed to dry.

A device is preferably placed in contact with a composition by dipping the medical device in the composition for a period of time ranging from about 30 seconds to about 180 minutes at a temperature ranging from about 25° C. to about 60° C. Preferably, a device is placed in contact with a composition by dipping the medical device in the composition for about 60 minutes at a temperature of about 37° C. A device is removed from a composition and then allowed to dry. A medical device may be placed in an oven or other heated environment for a period of time sufficient for a composition to dry.

Although one layer, or coating, of a composition is believed to provide a desired composition coating, multiple layers are preferred. Multiple layers of a composition are preferably applied to at least one surface of a medical device by repeating steps discussed above. Preferably, a medical device is contacted with a composition three times, allowing the composition to dry on at least one surface of the medical device prior to contacting the medical device with the composition for each subsequent layer. Thus, a medical device preferably includes three coats, or layers, of a composition on at least one surface of the medical device.

In another embodiment, a method for coating medical devices with a composition coating includes steps of forming a composition coating of an effective concentration to substantially prevent the growth or proliferation of biofilm embedded microorganisms on at least one surface of a medical device by dissolving an active component in an organic solvent, combining a medical device material penetrating agent to the active component(s) and organic solvent, and combining an alkalinizing agent to improve reactivity of the material of the medical device. A composition is then heated to a temperature ranging from about 30° C. to about 60° C. to enhance adherence of a composition coating to at least one surface of the device. A composition coating is applied to at least one surface of a medical device, preferably by contacting the composition coating to the at least one surface of the medical device for a sufficient period of time for the composition coating to adhere to at least one surface of the medical device. A medical device is removed from a composition coating and allowed to dry, preferably, for at least 18 hours at room temperature. A medical device may then be rinsed with a liquid, such as water and allowed to dry for at least 2 hours, and preferably 4 hours, before being sterilized. To facilitate drying of a composition of the invention onto a surface of a medical device, a medical device may be placed into a heated environment such as an oven.

In another aspect, the invention provides a method of incorporating a composition according to the invention into a device. Preferably, a device is a medical device and a composition is incorporated into a material forming the medical device during formation of the medical device. For example, a composition may be combined with a material forming the medical device, e.g., silicone, polyurethane, polyethylene, Gore-Tex® (polytetrafluoroethylene), Dacron® (polyethylene tetraphthalate), and Teflon® (polytetrafluoroethylene), and/or polypropylene, and extruded with the material forming the medical device, thereby incorporating the composition into material forming the medical device. In this embodiment, the composition may be incorporated in a septum or adhesive, which is placed at the medical device insertion or implantation site. One example of a medical device having a composition incorporated into the material forming the medical device in accordance with this embodiment is a catheter insertion seal having an adhesive layer described below in greater detail. Another example of a medical device having a composition incorporated into the material is an adhesive. A composition of the invention can be integrated into an adhesive, such as tape, thereby providing an adhesive, which may prevent growth or proliferation of biofilm embedded microorganisms on at least one surface of the adhesive.

Although the invention has been described with reference to illustrative embodiments, it is understood that the invention is not limited to these precise embodiments and that various changes and modifications may be effected therein by one skilled in the art. All changes and modifications are intended to be encompassed in the appended claims.

EXAMPLES

Example 1

Figure 2:
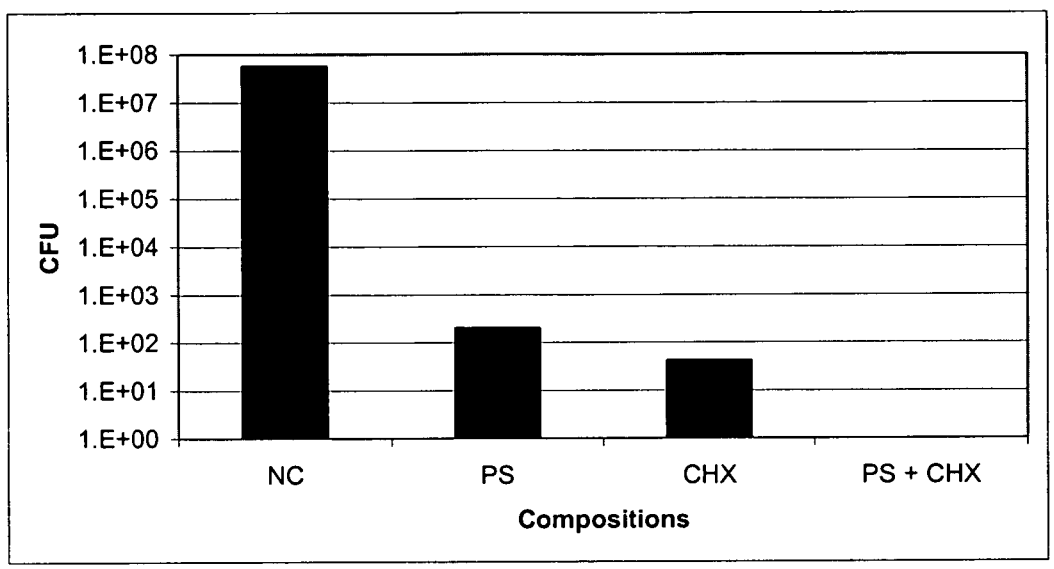
FIG. 2 is a bar graph illustrating the effect of a negative control (NC), 25 μg/ml protamine sulfate (PS), 25 μg/ml chlorhexidine salt (CHX), and a combination of 25 μg/ml protamine sulfate and 25 μg/ml chlorhexidine salt (PS+CHX) on the number (CFU) of biofilm embedded *Pseudomonas aeruginosa*.
Figure 3:
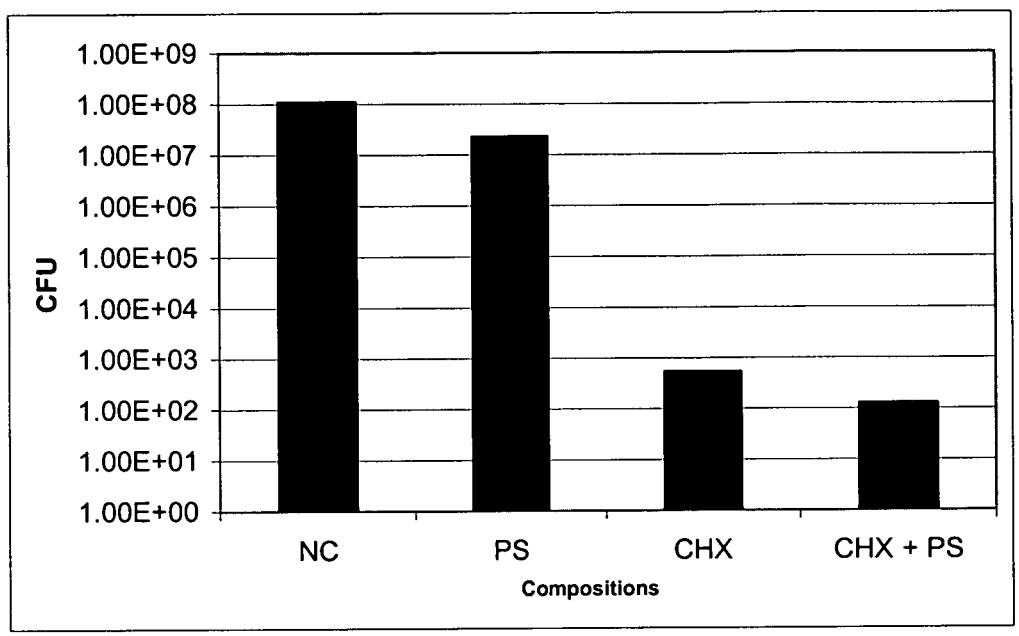
FIG. 3 is a bar graph illustrating the enhanced effect of a negative control, 12.5 μg/ml protamine sulfate (PS), 12.5 μg/ml chlorhexidine salt (CHX), and a combination of 12.5 μg/ml protamine sulfate and 12.5 μg/ml chlorhexidine salt (PS+CHX) on the number (CFU) of biofilm embedded *Staphylococcus epidermidis*.

Enhanced Effect of a Protamine Sulfate (PS) and Chlorhexidine Salt (CHX) Combination on Biofilm Embedded Catheter-Associated Bacteria In vitro microplate assays were performed to determine the enhanced effects of protamine sulfate and chlorhexidine salt combination on the growth of biofilm embedded biofilm forming catheter-associated bacteria such as *E. coli*, *Pseudomonas aeruginosa* and *Staphylococcus epidermidis*. Overnight culture of each bacterial strain grown in Luria-Bertani (LB) or Tryptic Soy Broth (TSB) was used as inoculum. Bacteria were grown in Colony Forming Antigen (CFA) medium (for gram-negative) or in TSB (for gram-positive) on a 12-well microplate in the absence and presence of each test compound (PS or CHX) separately and together (PS+CHX) at 12.5, 25, or 50 µg/ml. The plate was incubated at 37° C. for 24 hours. Media containing planktonic cells in each well were removed gently and rinsed with sterile water. A known volume of water was added to each well and sonicated for 30 seconds. The transfer of contents of each well into a sterile tube and vortexing for a minute was followed by 10-fold serial dilution and plating on agar plates using a spreader. After incubating the plates at 37° C. for 24 hours, the colonies forming units (CFU) were counted. Although chlorhexidine salt was more effective than protamine sulfate in inhibiting the growth of all three biofilm embedded test organisms, the combination of protamine sulfate and chlorhexidine salt had an enhanced inhibitory effect on *Pseudomonas aeruginosa* and *S. epidermidis* (FIGS. 1-3).

Example 2

Inhibitory Activity of Protamine Sulfate (PS) and Chlorhexidine Salt (CHX) Combination-Coated Silicone Catheter Against Catheter-Associated Bacteria The antimicrobial activity of PS+CHX coated and uncoated 1 cm silicone catheter sections were assessed using Kirby-Bauer technique as previously described by Sheretz et al. (*Antimicrob. Agents. Chemother.*, 33: 1174-1178, 1989). The catheters were coated by dipping in PS (100 mg/ml)+ CHX (400 mg/ml) solution followed by drying as described in U.S. Pat. No. 6,475,434. The catheters were gas-sterilized with ethylene oxide. Catheter-associated microorganisms such as *E. coli*, *Proteus mirabilis*, *Pseudomonas aeruginosa*, *Klebsiella pneumoniae*, *Enterococcus faecalis*, Vancomycin Resistant *Enterococci* (VRE), *Staphylococcus epidermidis*, *Staphylococcus aureus* and *Candida albicans* were grown in nutrient broth for 18 hours at 37° C. An appropriate inoculum of each bacterial or yeast strain was used to prepare spread plates. The coated and uncoated catheter sections were then carefully pressed into the center of each of the plates. Following incubation for 24 hours at 37° C., the zones of inhibition surrounding each of the sections were measured at the aspects of perpendicular to the long axes. The zone of inhibition varied from organism to organism ranging from 6 mm to 21 mm (Table 1). The coated catheter had a significant inhibitory activity against *E. coli*, *Staphylococcus epidermidis*, *Staphylococcus aureus*, and *Candida albicans*.

TABLE 1

Inhibitory activity of the protamine sulfate (PS) + chlorhexidine salt (CHX)-coated silicone catheter against catheter-associated microorganisms

| Organism | Inhibition Zone (mm) |
| --- | --- |
| E. coli | 14 ± 4.2 |
| Proteus mirabilis | 8 ± 0 |
| Pseudomonas aeruginosa | 6 ± 0 |
| Klebsiella pneumoniae | 10 ± 2.8 |
| Enterococcus faecalis | 13 ± 1.4 |
| Vancomycin Resistant Enterococci (VRE) | 13 ± 1.4 |
| Staphylococcus epidermidis | 19 ± 0 |
| Staphylococcus aureus | 21 ± 4.2 |
| Candida albicans | 16.5 ± 3.5 |

Example 3

Figure 4:
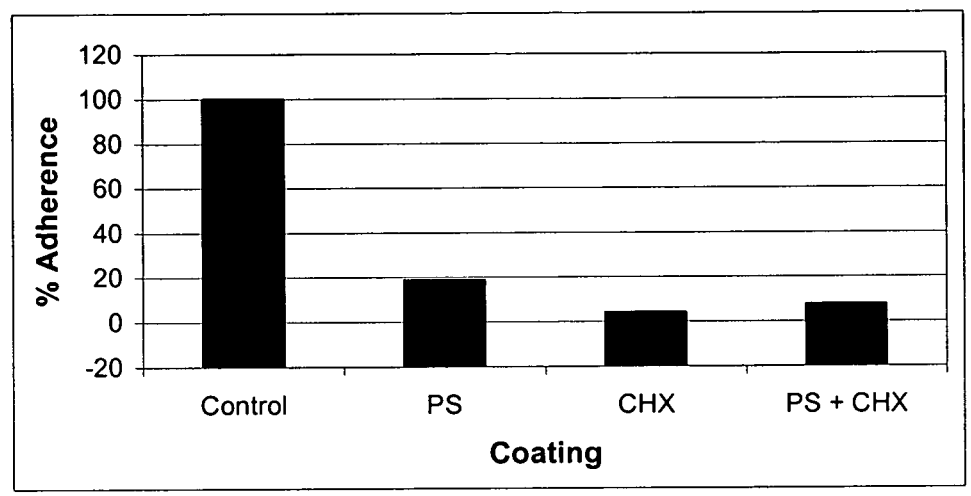
FIG. 4 is a bar graph illustrating the anti-adherence effects of silicone catheters coated with 100 mg/ml protamine sulfate (PS), 100 mg/ml chlorhexidine salt (CHX), and a combination of 100 mg/ml protamine sulfate and 100 mg/ml chlorhexidine salt (PS+CHX) on *E. coli*.
Figure 5:
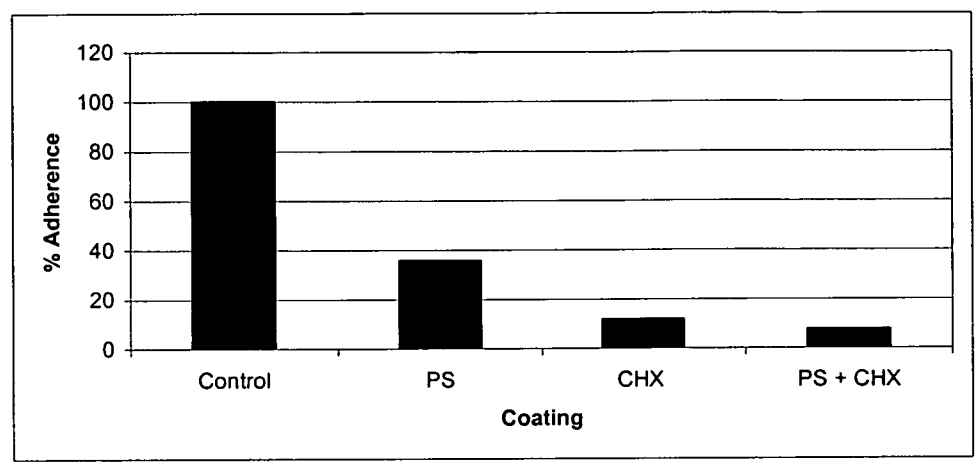
FIG. 5 is a bar graph illustrating the enhanced anti-adherence effect of silicone catheters coated with 100 mg/ml protamine sulfate (PS), 100 mg/ml chlorhexidine salt (CHX), and a combination of 100 mg/ml protamine sulfate and 100 mg/ml chlorhexidine salt (PS+CHX) on *Pseudomonas aeruginosa*.
Figure 6:
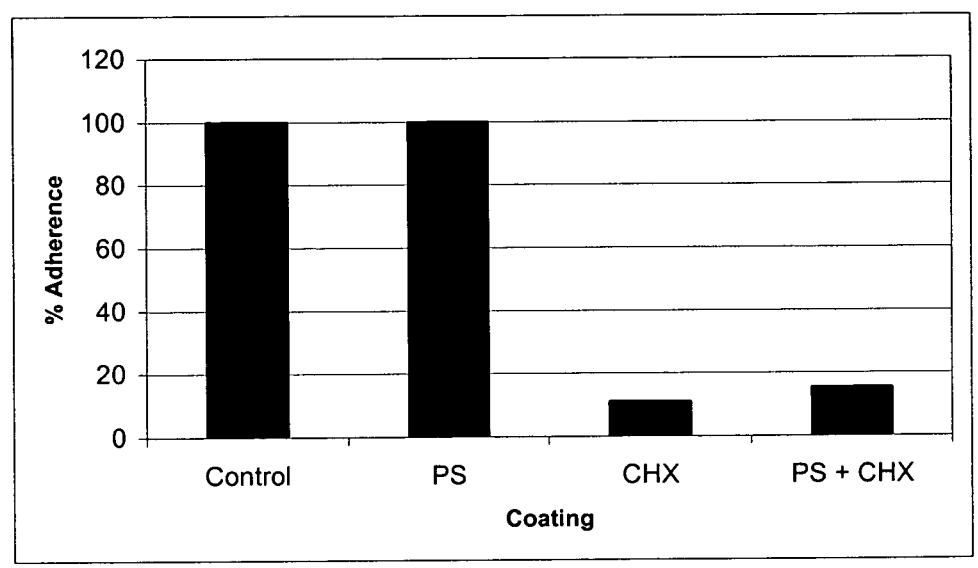
FIG. 6 is a bar graph illustrating the anti-adherence effect of the silicone catheters coated with 100 mg/ml protamine sulfate (PS), 100 mg/ml chlorhexidine salt (CHX), and a combination of 100 mg/ml protamine sulfate and 100 mg/ml chlorhexidine salt (PS+CHX) on *Staphylococcus epidermidis*.

Anti-Adherence Effect of Protamine Sulfate (PS) and Chlorhexidine Salt (CHX) Combination-Coated Silicone Catheter on Catheter-Associated Bacteria The ability of PS+CHX, PS, and CHX coated silicone catheters to resist bacterial colonization was tested by exposing uncoated and coated sections to *E. coli*, *Pseudomonas aeruginosa*, and *Staphylococcus epidermidis* in triplicate. The silicone catheters were coated with PS (100 mg/ml), CHX (100 mg/ml) and PS (100 mg/ml)+CHX (100 mg/ml), and gas-sterilized with ethylene oxide. The coated catheter sections were incubated in sterile artificial urine at 37° C. for 24 hours at 100 rpm prior to challenging with the bacteria. Following the incubation, the catheter sections were rinsed with sterile water and incubated in a bacterial culture in BHI medium at 37° C. for 3 hours at 100 rpm. After 3 hours of incubation, the sections were washed twice gently. Each washed section was transferred into a sterile tube containing 1 ml sterile water and subjected to sonication for 30 seconds followed by 1 minute vortexing. Further, each section was serially diluted using sterile water and plated on LB agar. The plates were incubated for 24 hours at 37° C. and the colonies (CFU) were counted. The CHX alone-coated catheter was superior to PS and PS+CHX coated catheters in inhibiting the adherence of *E. coli* and *S. epidermidis* (FIGS. 4 and 6). However, PS+CHX combination-coated catheter showed an enhanced anti-adherence effect against *P. aeruginosa* (FIG. 5).

Example 4

Durability of Inhibitory Activity of Protamine Sulfate (PS) and Chlorhexidine Salt (CHX) Combination-Coated Silicone Catheter The antimicrobial activity of PS+CHX coated 1 cm silicone catheter sections was assessed using Kirby-Bauer technique as previously described by Sheretz et al. (*Antimicrob. Agents. Chemother.*, 33:1174-1178, 1989). The catheters were coated by dipping in a PS (100 mg/ml)+CHX (400 mg/ml) solution followed by drying as described by in U.S. Pat. No. 6,475,434. The catheter sections were gas-sterilized with ethylene oxide. Catheter-associated microorganisms such as *E. coli*, *Proteus mirabilis*, *Pseudomonas aeruginosa*, *Klebsiella pneumoniae*, *Enterococcus faecalis*, Vancomycin Resistant *Enterococci* (VRE), *Staphylococcus epidermidis*, *Staphylococcus aureus*, and *Candida albicans* were grown in nutrient broth for 18 hours at 37° C. An appropriate inoculum of each bacterial strain was used to prepare spread plates. The coated catheter sections were then carefully pressed into the center of each of the plates. Following incubation for 24 hours at 37° C., the zones of inhibition surrounding each of the sections were measured at the aspects of perpendicular to the long axes. After measuring the zones of inhibition, the sections were transferred onto fresh spread plates inoculated with respective test organism and incubated for 24 hours at 37° C. again. The zones of inhibition surrounding each of the sections were measured again. This procedure was repeated for determining the durability of inhibitory activity of coated catheter sections for 3 days, 7 days and 10 days with each test organism. The inhibitory activity of coated catheter sections against *Klebsiella pneumoniae*, VRE, and *Pseudomonas aeruginosa* lasted for only 3 days (Table 2). However, the coated catheter sections showed a significant inhibitory activity against E. coli, Staphylococcus epidermidis, Staphylococcus aureus, and Candida albicans even after 10 days of passage.

TABLE 2

Durability of inhibitory activity of the protamine sulfate (PS) + chlorhexidine salt (CHX)-coated silicone catheter segments

| Organism | Inhibition Zone (mm) | | | | |
|---|---|---|---|---|---|
| | Day 0 | Day 1 | Day 3 | Day 7 | Day 10 |
| E. coli | 14 | 10 | 11 | 10 | 8 |
| Proteus mirabilis | 8 | 0 | 0 | 0 | 0 |
| Pseudomonas aeruginosa | 6 | 6 | 11 | 0 | 0 |
| Klebsiella pneumoniae | 10 | 6 | 6 | 0 | 8 |
| Enterococcus faecalis | 13 | 8 | 9 | 6 | 6 |
| Vancomycin Resistant Enterococci (VRE) | 13 | 9 | 9 | 7 | 0 |
| Staphylococcus epidermidis | 19 | 16 | 13 | 15 | 12 |
| Staphylococcus aureus | 21 | 13 | 14 | 8 | 10 |
| Candida albicans | 17 | 13 | 8 | 8 | 8 |

Example 5

Figure 7:
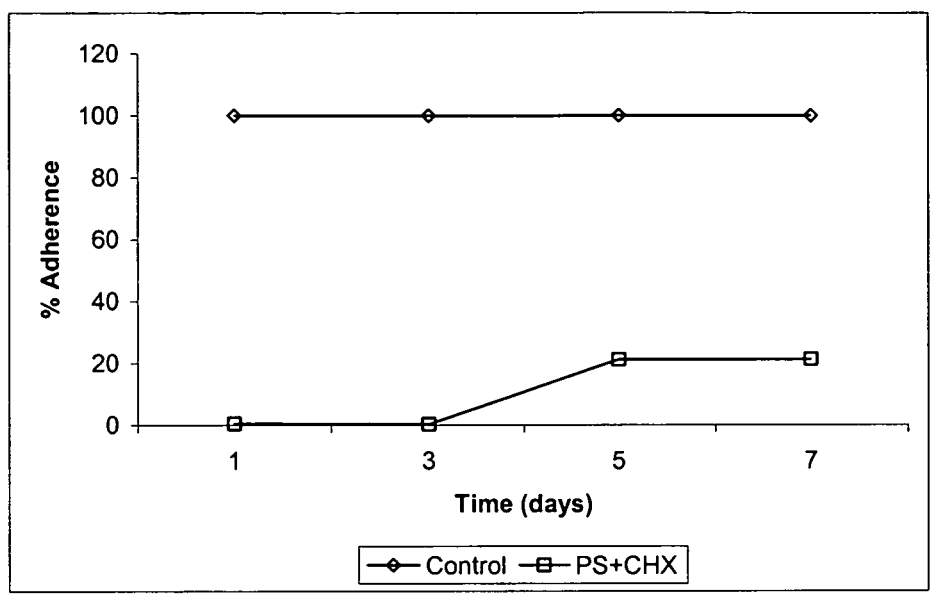
FIG. 7 is a line graph illustrating the durability of anti-adherence activity of 100 mg/ml protamine sulfate (PS) and 400 mg/ml chlorhexidine salt (CHX) coated silicone catheter against *E. coli*.
Figure 8:
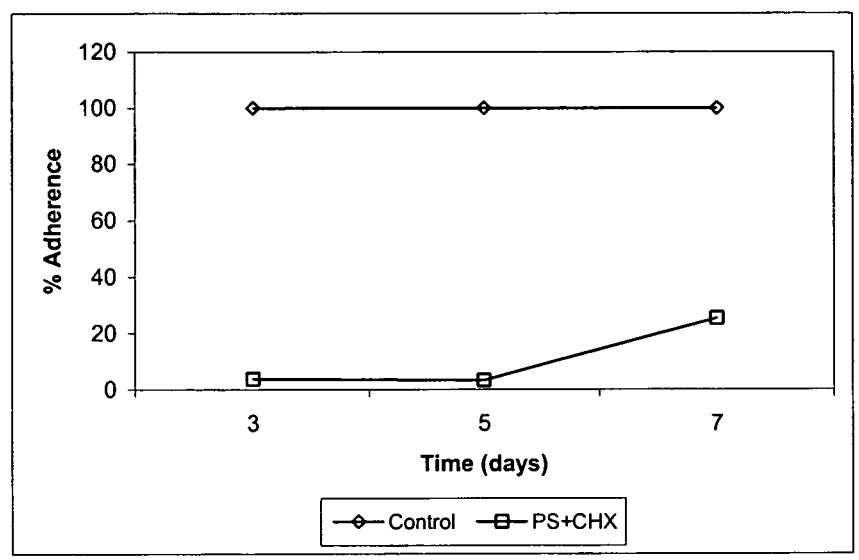
FIG. 8 is a line graph illustrating the durability of anti-adherence activity of 100 mg/ml protamine sulfate (PS) and 400 mg/ml chlorhexidine salt (CHX) coated silicone catheters against *Staphylococcus epidermidis*.

Durability of Anti-Adherence Activity of Protamine Sulfate (PS) and Chlorhexidine Salt (CHX) Combination-Coated Silicone Catheter The ability of PS+CHX coated silicone catheters to resist bacterial colonization for a period of 7 days was tested by exposing uncoated and coated sections (in duplicate) to E. coli and Staphylococcus epidermidis. The silicone catheters were coated with PS (100 mg/ml)+CHX (400 mg/ml), and gas-sterilized with ethylene oxide. The coated and uncoated catheter sections were incubated in sterile artificial urine at 37° C. separately for 7 days at 100 rpm prior to challenging with the bacteria. Artificial urine in the flask was replaced with fresh artificial urine every 24 hours. Both coated and uncoated catheter segments (in triplicate) were removed at time intervals of 1, 3, 5, and 7 days and gently rinsed with sterile water. Further, they were challenged with the above test organisms one at a time. Following the incubation, the catheter sections were rinsed 3 times gently with sterile water and incubated in a test organism's culture broth at 37° C. for 3 hours at 100 rpm. After 3 hours of incubation, the sections were washed twice gently. Each washed segment was transferred into a sterile tube containing 1 ml sterile water and subjected to sonication for 30 seconds followed by 1 minute vortexing. Further, each section was serially diluted using sterile water and plated on LB agar. The plates were incubated for 24 hours at 37° C. and the colonies forming units (CFU) were counted. This procedure was repeated for each time interval. The PS+CHX coated catheter sections were effective in preventing bacterial cells adhering, as about 80% inhibition of adherence of both bacterial strains at day 7 was observed (FIGS. 7-8).

Example 6

In Vivo Efficacy of Protamine Sulfate (PS) and Chlorhexidine Salt (CHX) Combination-Coated Silicone Catheter An in vivo efficacy study was conducted using a previously reported rabbit model with slight modifications (Darouiche, et al., J. Heart. Valve. Dis., 11:99-104, 2002). This preliminary study was to assess the in vivo efficacy of silicone catheter coated with PS (100 mg/ml)+CHX (400 mg/ml) in preventing E. coli infection of subcutaneously implanted segments of silicone catheters. The silicone catheters were coated with PS (100 mg/ml)+CHX (400 mg/ml), and gas-sterilized with ethylene oxide. A total of 15 uncoated 1-cm segments of silicone catheters and 15 coated catheter segments were implanted subcutaneously in the back of a total of 4 rabbits that had received a single dose of vancomycin (20 mg/kg body weight) for prophylaxis against gram-positive skin microflora. Each device was inoculated with 50 µl of $2 \times 10^4$ CFU/ml of clinical isolate of E. coli and wounds were then closed. 2 mg/kg body weight of ketoprofen was injected into each rabbit intramuscularly (IM) daily as an anti-inflammatory/analgesic. After 7 days, the four rabbits were sacrificed. The devices were explanted and cultured by using the sonication technique and plating. Swab cultures were obtained from surrounding fluid collections. Although 3 out of 15 (20%) uncoated segments were colonized by E. coli, all 15-coated segments were completely free from bacterial colonization (Table 3).

TABLE 3

In vivo efficacy of protamine sulfate (PS) and chlorhexidine salt (CHX)-coated silicone catheter

| Test Group | No. of Rabbits | No. of Segments Implanted | % Infection (after 7 days) |
|---|---|---|---|
| Control | 1 | 4 uncoated | 20 |
| | 2 | 4 uncoated | |
| | 3 | 4 uncoated | |
| | 4 | 3 uncoated | |
| Experimental | 1 | 4 coated | 0 |
| | 2 | 4 coated | |
| | 3 | 4 coated | |
| | 4 | 3 coated | |

Example 7

In Vivo Efficacy of Silicone Bladder Catheters Coated with Chlorhexidine/Protamine The objectives of this Example were to: (1) confirm the in vivo efficacy of catheters coated with chlorhexidine/protamine as compared with uncoated catheters, (2) to compare the rates of device colonization and device-related infections by E. coli for catheters coated with chlorhexidine/protamine vs. catheters coated with hydrogel-silver, (3) to show that catheters coated with chlorhexidine/protamine were useful for preventing growth or proliferation of biofilm embedded microorganisms and, and (4) to show that catheters coated with chlorhexidine/protamine were useful in protecting against device-related infection.

An animal study was done using an established model of E. coli infection of medical devices inserted subcutaneously in the back of rabbits. Female New Zealand white, specific pathogen-free rabbits (body weight 2-3 kg) were anesthetized by receiving intramuscular injection (0.5 ml/kg body weight) of a mixture of ketamine (70 mg/kg body weight) and acepromazine (2 mg/kg body weight). To simulate the practice of administering perioperative antibiotic prophylaxis in human patients, each animal received immediately after induction of anesthesia an intramuscular injection of vancomycin (20 mg/kg) that was active against gram-positive organisms but not against E. coli. The backs of rabbits were shaved, then prepared and draped in a sterile fashion. Six (2 chlorhexidine/ protamine-coated, 2 hydrogel-silver-coated, and 2 uncoated) 2-cm long catheter segments were subcutaneously inserted 3-4 cm lateral to the spine and away from each other. A total of 84 devices were placed in 14 rabbits. $10^5$ CFU of pathogenic of *E. coli* strain 2131 (a clinical isolate from a patient with catheter-related UTI) was inoculated onto the surface of inserted device and wounds were sutured. Rabbits were monitored daily for signs of local infection, sepsis, or major distress. Rabbits were sacrificed at 1 week and the following studies were done:

a. Quantitative cultures from devices by using the sonication technique, and b. Qualitative swab culture of the site adjacent to the device.

The two primary outcomes of the study were device colonization (defined as growth of *E. coli* from quantitative sonication culture; detectability limit, 10 CFU) and device-related infection (defined as device colonization plus growth of *E. coli* from qualitative swab culture of the site surrounding the device). The rates of device colonization and device-related infection were compared between the different groups by using a 2-tailed Fisher's exact test with 90% power. A P value of ≤0.05 indicated significant differences.

The secondary outcome of the mean bacterial CFU retrieved from removed catheters was compared between the three groups by using the two-sample T test with unequal variance. A P value of ≤0.05 indicated significant differences.

Two of 28 (7%) chlorhexidine/protamine-coated catheters, 25 of 28 (89%) silver/hydrogel-coated catheters, and 18 of 28 (64%) uncoated catheters became colonized with *E. coli*. The chlorhexidine/protamine-coated catheters were significantly less likely to be colonized than either silver/hydrogel-coated catheters (P<0.001) or uncoated catheters (P=0.0016). There was no significant difference (P=0.51) in the rate of colonization of silver/hydrogel-coated vs. uncoated catheters.

One of 28 (4%) chlorhexidine/protamine-coated catheters, 12 of 28 (43%) silver/hydrogel-coated catheters, and 14 of 28 (50%) uncoated catheters developed device-related infection due to *E. coli*. The chlorhexidine/protamine-coated catheters were significantly less likely to cause device-related infection than either silver/hydrogel-coated catheters (P=0.046) or uncoated catheters (P=0.013). There was no significant difference (P=1.69) in the rate of device-related infection between the silver/hydrogel-coated vs. uncoated catheters.

The mean number of CFU was $4.6 \times 10^5$ in the chlorhexidine/protamine group, $2.5 \times 10^6$ in the silver-hydrogel group, and $8.3 \times 10^6$ in the uncoated group. The mean number of CFU was significantly lower (P=0.031) on the surfaces of chlorhexidine/protamine-coated catheters than uncoated catheters. There were no significant differences in the mean number of cfu when comparing silver/hydrogel-coated catheters with either chlorhexidine/protamine-coated catheters (P=0.22) or uncoated catheters (P=0.13).

These results (Table 4) show that coating of catheters with chlorhexidine/protamine but not with silver/hydrogel protects against device colonization and device-related infection. The minimum detectability for device cultures was 10 CFU per device. 50 µl of $2 \times 10^6$ CFU/ml or $1 \times 10^5$ CFU of absolute inoculum was used. 2 mg/kg of ketoprofen was injected in each rabbit IM daily as an anti-inflammatory/analgesic. 20 mg/kg of vancomycin was given pre-operatively as a prophylactic antibiotic. External diameter of the silicone urinary catheter was 4 mm. 2 cm segments of uncoated catheters were used. The cultures from the blood drawn prior to sacrificing rabbits were all negative.

TABLE 4

In-vivo Activity of Antimicrobial Coated Urinary Silicone Catheters against *E. coli* strain 2131.

| Device | No. of days implanted | Device treatment | Device culture (total cfu) | Site swab (total cfu) |
|---|---|---|---|---|
| 5-3 | 7 | PA/CH | 0 | − |
| 5-4 | 7 | PA/CH | 0 | − |
| 6-1 | 7 | PA/CH | 0 | − |
| 6-6 | 7 | PA/CH | 0 | − |
| 7-2 | 7 | PA/CH | 0 | − |
| 7-5 | 7 | PA/CH | 0 | − |
| 8-2 | 7 | PA/CH | 0 | − |
| 8-5 | 7 | PA/CH | 0 | − |
| 9-3 | 7 | PA/CH | 0 | − |
| 9-4 | 7 | PA/CH | 0 | − |
| 10-1 | 7 | PA/CH | 0 | − |
| 10-6 | 7 | PA/CH | 0 | − |
| 11-2 | 7 | PA/CH | $1.7 \times 10^2$ | − |
| 11-5 | 7 | PA/CH | 0 | − |
| 12-3 | 7 | PA/CH | 0 | − |
| 12-4 | 7 | PA/CH | 0 | − |
| 13-1 | 7 | PA/CH | 0 | − |
| 13-6 | 7 | PA/CH | 0 | − |
| 14-2 | 7 | PA/CH | 0 | − |
| 14-5 | 7 | PA/CH | 0 | − |
| 15-3 | 7 | PA/CH | 0 | − |
| 15-4 | 7 | PA/CH | 0 | + |
| 16-2 | 7 | PA/CH | 0 | − |
| 16-5 | 7 | PA/CH | 0 | − |
| 17-3 | 7 | PA/CH | $1.3 \times 10^7$ | + |
| 17-4 | 7 | PA/CH | 0 | − |
| 18-1 | 7 | PA/CH | 0 | − |
| 18-6 | 7 | PA/CH | 0 | − |
| 5-2 | 7 | Ag | $4.2 \times 10^6$ | + |
| 5-5 | 7 | Ag | $2.4 \times 10^6$ | + |
| 6-3 | 7 | Ag | $7.7 \times 10^2$ | + |
| 6-4 | 7 | Ag | $8.2 \times 10^4$ | + |
| 7-3 | 7 | Ag | $7.0 \times 10^1$ | − |
| 7-4 | 7 | Ag | $4.4 \times 10^7$ | + |
| 8-1 | 7 | Ag | $3.6 \times 10^3$ | − |
| 8-6 | 7 | Ag | $1.4 \times 10^6$ | + |
| 9-1 | 7 | Ag | $2.0 \times 10^6$ | + |
| 9-6 | 7 | Ag | $3.8 \times 10^6$ | − |
| 10-2 | 7 | Ag | $1.9 \times 10^5$ | − |
| 10-5 | 7 | Ag | 0 | − |
| 11-3 | 7 | Ag | $5.6 \times 10^6$ | − |
| 11-4 | 7 | Ag | $1.0 \times 10^4$ | − |
| 12-2 | 7 | Ag | $4.2 \times 10^2$ | − |
| 12-5 | 7 | Ag | $1.4 \times 10^2$ | − |
| 13-2 | 7 | Ag | $6.8 \times 10^5$ | + |
| 13-5 | 7 | Ag | $1.8 \times 10^6$ | + |
| 14-3 | 7 | Ag | 0 | − |
| 14-4 | 7 | Ag | $2.5 \times 10^3$ | − |
| 15-1 | 7 | Ag | $4.3 \times 10^3$ | − |
| 15-6 | 7 | Ag | $3.1 \times 10^4$ | − |
| 16-1 | 7 | Ag | $2.5 \times 10^5$ | + |
| 16-6 | 7 | Ag | $1.1 \times 10^6$ | + |
| 17-2 | 7 | Ag | $1.8 \times 10^6$ | + |
| 17-5 | 7 | Ag | $1.8 \times 10^5$ | − |
| 18-3 | 7 | Ag | 0 | − |
| 18-4 | 7 | Ag | $1.3 \times 10^3$ | − |
| 5-1 | 7 | Uncoated | $2.4 \times 10^7$ | + |
| 5-6 | 7 | Uncoated | $3.6 \times 10^7$ | + |
| 6-2 | 7 | Uncoated | $1.5 \times 10^3$ | + |
| 6-5 | 7 | Uncoated | $6.4 \times 10^4$ | + |
| 7-1 | 7 | Uncoated | $5.6 \times 10^5$ | + |
| 7-6 | 7 | Uncoated | $7.8 \times 10^7$ | + |
| 8-3 | 7 | Uncoated | 0 | − |
| 8-4 | 7 | Uncoated | 0 | − |
| 9-2 | 7 | Uncoated | $1.6 \times 10^5$ | − |
| 9-5 | 7 | Uncoated | $1.6 \times 10^4$ | + |
| 10-3 | 7 | Uncoated | $4.0 \times 10^1$ | − |
| 10-4 | 7 | Uncoated | 0 | − |
| 11-1 | 7 | Uncoated | $7.6 \times 10^6$ | + |
| 11-6 | 7 | Uncoated | $4.2 \times 10^7$ | + |
| 12-1 | 7 | Uncoated | 0 | − |
| 12-6 | 7 | Uncoated | $2.3 \times 10^7$ | + |
| 13-3 | 7 | Uncoated | 0 | − |
| 13-4 | 7 | Uncoated | 0 | − |

TABLE 4-continued

In-vivo Activity of Antimicrobial Coated Urinary Silicone Catheters against *E. coli* strain 2131.

| Device | No. of days implanted | Device treatment | Device culture (total cfu) | Site swab (total cfu) |
|---|---|---|---|---|
| 14-1 | 7 | Uncoated | $2.5 \times 10^5$ | + |
| 14-6 | 7 | Uncoated | 0 | − |
| 15-2 | 7 | Uncoated | 0 | − |
| 15-5 | 7 | Uncoated | $1.0 \times 10^2$ | + |
| 16-3 | 7 | Uncoated | $6.7 \times 10^2$ | − |
| 16-4 | 7 | Uncoated | $3.0 \times 10$ | − |
| 17-1 | 7 | Uncoated | $2.0 \times 10^7$ | + |
| 17-6 | 7 | Uncoated | $7.0 \times 10^5$ | + |
| 18-2 | 7 | Uncoated | 0 | − |
| 18-5 | 7 | Uncoated | 0 | − |

I claim:

1. An insertable or implantable medical device comprising a coated external surface of said medical device, wherein said coated external surface comprises at least two layers of a composition comprising (a) protamine sulfate and (b) chlorhexidine or a salt thereof.

2. The medical device according to claim 1 prepared by a process comprising:
   a) contacting the external surface of the medical device with a solution of i) about 10 mg/ml to about 200 mg/ml of protamine sulfate and ii) about 100 mg/ml to about 400 mg/ml of chlorhexidine or a salt thereof;
   b) drying the medical device; and
   c) sterilizing the medical device.

3. The medical device according to claim 1, wherein the chlorhexidine salt is selected from the group consisting of chlorhexidine digluconate, chlorhexidine diacetate, and chlorhexidine dihydrochloride.

4. The medical device according to claim 1, further comprising at least one ingredient selected from the group consisting of: a binding, bonding, or coupling agent; a bis-phenol; a quaternary ammonium compound; a maleimide; an antibiotic; and a pH adjuster.

5. The medical device of claim 1, wherein the medical device is an indwelling catheter.

6. The medical device of claim 5, wherein the indwelling catheter is a central venous catheter, dialysis catheter, long term tunneled central venous catheters, short-term central venous catheters, peripherally inserted central catheters, peripheral venous catheters, pulmonary artery Swan-Ganz catheters, urinary catheters, or peritoneal catheter.

7. The medical device of claim 1, where the medical device is a long-term urinary device, tissue bonding urinary device, vascular catheter port, wound drain tube, hydrocephalus shunt, heart valve, heart assist device, cannula, intravenous tube, breathing tube, feeding tube, or orthopedic implant.

8. An implantable or insertable medical device comprising (a) protamine sulfate and (b) chlorhexidine or a salt thereof incorporated into an external surface of said medical device.

9. The medical device according to claim 8, wherein the chlorhexidine salt is selected from the group consisting of chlorhexidine digluconate, chlorhexidine diacetate, and chlorhexidine dihydrochloride.

10. The medical device according to claim 8, further comprising at least one ingredient selected from the group consisting of: a binding, bonding, or coupling agent; a bis-phenol; a quaternary ammonium compound; a maleimide; an antibiotic; and a pH adjuster.

11. The medical device of claim 8, wherein the medical device is an indwelling catheter.

12. The medical device of claim 11, wherein the indwelling catheter is a central venous catheter, dialysis catheter, long term tunneled central venous catheters, short-term central venous catheters, peripherally inserted central catheters, peripheral venous catheters, pulmonary artery Swan-Ganz catheters, urinary catheters, or peritoneal catheter.

13. The medical device of claim 8, where the medical device is a long-term urinary device, tissue bonding urinary device, vascular catheter port, wound drain tube, hydrocephalus shunt, heart valve, heart assist device, cannula, intravenous tube, breathing tube, feeding tube, or orthopedic implant.

* * * * *